(12) United States Patent
Garrison

(10) Patent No.: US 12,029,404 B2
(45) Date of Patent: **\*Jul. 9, 2024**

(54) VESSEL ACCESS AND CLOSURE ASSIST SYSTEM AND METHOD

(71) Applicant: Silk Road Medical, Inc., Sunnyvale, CA (US)

(72) Inventor: Michi E. Garrison, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 199 days.

This patent is subject to a terminal disclaimer.

(21) Appl. No.: 17/220,718

(22) Filed: Apr. 1, 2021

(65) Prior Publication Data

US 2021/0290213 A1    Sep. 23, 2021

Related U.S. Application Data

(63) Continuation of application No. 16/250,825, filed on Jan. 17, 2019, now Pat. No. 10,973,502, which is a
(Continued)

(51) Int. Cl.
*A61B 17/00* (2006.01)
*A61B 17/10* (2006.01)
(Continued)

(52) U.S. Cl.
CPC ........ *A61B 17/0057* (2013.01); *A61B 17/105* (2013.01); *A61B 2017/00477* (2013.01);
(Continued)

(58) Field of Classification Search
CPC .............. A61B 17/0057; A61B 17/105; A61B 2017/00477; A61B 2017/00584;
(Continued)

(56) References Cited

U.S. PATENT DOCUMENTS 4,301,803 A    11/1981    Handa et al.
4,493,707 A    1/1985    Ishihara
(Continued)

FOREIGN PATENT DOCUMENTS

EP    0 669 103 A1    8/1995
JP    S59-161808 U    10/1984
(Continued)

OTHER PUBLICATIONS

Bergeron et al. (2008) MEET Presentation, Cannes, French Riviera "Why I do not use routine femoral access for CAS." 12 pages.
(Continued)

*Primary Examiner* — Richard G Louis
(74) *Attorney, Agent, or Firm* — Mintz Levin Cohn Ferris Glovsky and Popeo, P.C.

(57) ABSTRACT

A vessel access and closure assist system is used for accessing a vessel to perform a vascular intervention. The system facilitates the delivery of a vessel closure device onto a blood vessel for closing an opening in the wall of the blood vessel. The vessel access and closure assist system includes a procedural introducer sheath that directly couples to a vessel closure device delivery sheath such that the procedural introducer sheath does not have to be exchanged with the vessel closure device delivery sheath.

9 Claims, 8 Drawing Sheets

Related U.S. Application Data continuation of application No. 14/710,400, filed on May 12, 2015, now Pat. No. 10,182,801.

(60) Provisional application No. 62/074,964, filed on Nov. 4, 2014, provisional application No. 61/994,623, filed on May 16, 2014.

(51) Int. Cl.
  *A61B 17/064* (2006.01)
  *A61M 25/06* (2006.01)
  *A61M 29/00* (2006.01)

(52) U.S. Cl.
  CPC .............. *A61B 2017/00584* (2013.01); *A61B 2017/00623* (2013.01); *A61B 2017/00668* (2013.01); *A61B 2017/0645* (2013.01); *A61M 25/0662* (2013.01); *A61M 29/00* (2013.01)

(58) Field of Classification Search
  CPC ........... A61B 2017/00623; A61B 2017/00668; A61B 2017/0645; A61M 25/0662; A61M 29/00
  See application file for complete search history.

(56) References Cited

U.S. PATENT DOCUMENTS

| | | |
|---|---|---|
| 5,007,921 A | 4/1991 | Brown |
| 5,026,390 A | 6/1991 | Brown |
| 5,304,184 A | 4/1994 | Hathaway et al. |
| 5,306,250 A | 4/1994 | March et al. |
| 5,403,328 A | 4/1995 | Shallman |
| 5,417,699 A | 5/1995 | Klein et al. |
| 5,443,454 A | 8/1995 | Tanabe et al. |
| 5,476,469 A | 12/1995 | Hathaway et al. |
| 5,520,702 A | 5/1996 | Sauer et al. |
| 5,527,322 A | 6/1996 | Klein et al. |
| 5,549,633 A | 8/1996 | Evans et al. |
| 5,584,803 A | 12/1996 | Stevens et al. |
| 5,613,974 A | 3/1997 | Andreas et al. |
| 5,643,289 A | 7/1997 | Sauer et al. |
| 5,643,292 A | 7/1997 | Hart |
| 5,649,959 A * | 7/1997 | Hannam ............ A61B 17/0057 604/93.01 |
| 5,669,917 A | 9/1997 | Sauer et al. |
| 5,674,231 A | 10/1997 | Green et al. |
| 5,720,757 A | 2/1998 | Hathaway et al. |
| 5,746,755 A | 5/1998 | Wood et al. |
| 5,766,183 A | 6/1998 | Sauer |
| 5,769,830 A | 6/1998 | Parker |
| 5,779,719 A | 7/1998 | Klein et al. |
| 5,782,800 A | 7/1998 | Yoon |
| 5,792,152 A | 8/1998 | Klein et al. |
| 5,797,929 A | 8/1998 | Andreas et al. |
| 5,810,846 A | 9/1998 | Virnich et al. |
| 5,810,850 A | 9/1998 | Hathaway et al. |
| 5,833,650 A | 11/1998 | Imran |
| 5,860,990 A | 1/1999 | Nobles et al. |
| 5,860,991 A | 1/1999 | Klein et al. |
| 5,902,311 A | 5/1999 | Andreas et al. |
| 5,916,193 A | 6/1999 | Stevens et al. |
| 5,921,994 A | 7/1999 | Andreas et al. |
| 6,004,341 A | 12/1999 | Zhu et al. |
| 6,024,747 A | 2/2000 | Kontos |
| 6,030,395 A | 2/2000 | Nash et al. |
| 6,036,699 A | 3/2000 | Andreas et al. |
| 6,042,601 A | 3/2000 | Smith |
| 6,077,279 A | 6/2000 | Kontos |
| 6,110,185 A | 8/2000 | Barra et al. |
| 6,117,144 A | 9/2000 | Nobles et al. |
| 6,117,145 A | 9/2000 | Wood et al. |
| 6,132,440 A | 10/2000 | Hathaway et al. |
| 6,136,010 A | 10/2000 | Modesitt et al. |
| 6,146,370 A | 11/2000 | Barbut |
| 6,146,373 A | 11/2000 | Cragg et al. |
| 6,190,396 B1 | 2/2001 | Whitin et al. |
| 6,197,042 B1 | 3/2001 | Ginn et al. |
| 6,206,868 B1 | 3/2001 | Parodi |
| 6,206,893 B1 | 3/2001 | Klein et al. |
| 6,245,079 B1 | 6/2001 | Nobles et al. |
| 6,277,140 B2 | 8/2001 | Ginn et al. |
| 6,295,989 B1 | 10/2001 | Connors, III |
| 6,302,898 B1 | 10/2001 | Edwards et al. |
| 6,306,163 B1 | 10/2001 | Fitz |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,364,900 B1 | 4/2002 | Heuser |
| 6,368,334 B1 | 4/2002 | Sauer |
| 6,379,325 B1 | 4/2002 | Benett et al. |
| 6,391,048 B1 | 5/2002 | Ginn et al. |
| 6,413,235 B1 | 7/2002 | Parodi |
| 6,423,032 B2 | 7/2002 | Parodi |
| 6,423,086 B1 | 7/2002 | Barbut et al. |
| 6,428,549 B1 | 8/2002 | Kontos |
| 6,435,189 B1 | 8/2002 | Lewis et al. |
| 6,436,109 B1 | 8/2002 | Kontos |
| 6,454,741 B1 | 9/2002 | Muni et al. |
| 6,461,364 B1 | 10/2002 | Ginn et al. |
| 6,482,172 B1 | 11/2002 | Thramann |
| 6,517,553 B2 | 2/2003 | Klein et al. |
| 6,533,800 B1 | 3/2003 | Barbut |
| 6,540,712 B1 | 4/2003 | Parodi et al. |
| 6,551,331 B2 | 4/2003 | Nobles et al. |
| 6,558,399 B1 | 5/2003 | Isbell et al. |
| 6,562,049 B1 | 5/2003 | Norlander et al. |
| 6,562,052 B2 | 5/2003 | Nobles et al. |
| 6,569,182 B1 | 5/2003 | Balceta et al. |
| 6,582,448 B1 | 6/2003 | Boyle et al. |
| 6,589,214 B2 | 7/2003 | McGuckin, Jr. et al. |
| 6,595,953 B1 | 7/2003 | Coppi et al. |
| 6,596,003 B1 | 7/2003 | Realyvasquez, Jr. et al. |
| 6,623,471 B1 | 9/2003 | Barbut |
| 6,623,510 B2 | 9/2003 | Carley et al. |
| 6,626,886 B1 | 9/2003 | Barbut |
| 6,626,918 B1 | 9/2003 | Ginn et al. |
| 6,632,238 B2 | 10/2003 | Ginn et al. |
| 6,641,592 B1 | 11/2003 | Sauer et al. |
| 6,645,222 B1 | 11/2003 | Parodi et al. |
| 6,652,480 B1 | 11/2003 | Imran et al. |
| 6,663,650 B2 | 12/2003 | Sepetka et al. |
| 6,679,893 B1 | 1/2004 | Tran |
| 6,682,505 B2 | 1/2004 | Bates et al. |
| 6,695,867 B2 | 2/2004 | Ginn et al. |
| 6,719,717 B1 | 4/2004 | Johnson et al. |
| 6,719,777 B2 | 4/2004 | Ginn et al. |
| 6,730,102 B1 | 5/2004 | Burdulis, Jr. et al. |
| 6,746,457 B2 | 6/2004 | Dana et al. |
| 6,749,621 B2 | 6/2004 | Pantages et al. |
| 6,790,197 B2 | 9/2004 | Kosinski et al. |
| 6,837,881 B1 | 1/2005 | Barbut |
| 6,840,949 B2 | 1/2005 | Barbut |
| 6,847,234 B2 | 1/2005 | Choi |
| 6,855,136 B2 | 2/2005 | Dorros et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,908,474 B2 | 6/2005 | Hogendijk et al. |
| 6,932,824 B1 | 8/2005 | Roop et al. |
| 6,936,060 B2 | 8/2005 | Hogendijk et al. |
| 6,942,674 B2 | 9/2005 | Belef et al. |
| 6,958,059 B2 | 10/2005 | Zadno-Azizi |
| 6,964,668 B2 | 11/2005 | Modesitt et al. |
| 7,001,398 B2 | 2/2006 | Carley et al. |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,029,480 B2 | 4/2006 | Klein et al. |
| 7,029,487 B2 | 4/2006 | Greene, Jr. et al. |
| 7,033,344 B2 | 4/2006 | Imran |
| 7,048,747 B2 | 5/2006 | Arcia et al. |
| 7,048,758 B2 | 5/2006 | Boyle et al. |
| 7,063,714 B2 | 6/2006 | Dorros et al. |

(56) References Cited

U.S. PATENT DOCUMENTS

| | | |
|---|---|---|
| 7,083,594 B2 | 8/2006 | Coppi |
| 7,090,686 B2 | 8/2006 | Nobles et al. |
| 7,094,246 B2 | 8/2006 | Anderson et al. |
| 7,144,411 B2 | 12/2006 | Ginn et al. |
| 7,208,008 B2 | 4/2007 | Clarke |
| 7,232,452 B2 | 6/2007 | Adams et al. |
| 7,367,982 B2 | 5/2008 | Nash et al. |
| 7,374,561 B2 | 5/2008 | Barbut |
| 7,390,328 B2 | 6/2008 | Modesitt |
| 7,396,359 B1 | 7/2008 | Derowe et al. |
| 7,422,579 B2 | 9/2008 | Wahr et al. |
| 7,458,980 B2 | 12/2008 | Barbut |
| 8,157,760 B2 | 4/2012 | Criado et al. |
| 8,545,432 B2 | 10/2013 | Renati et al. |
| 10,039,906 B2 | 8/2018 | Kume et al. |
| 10,085,864 B2 | 10/2018 | Chou et al. |
| 10,159,479 B2 | 12/2018 | Hentges et al. |
| 10,182,801 B2 | 1/2019 | Garrison |
| 2001/0003158 A1* | 6/2001 | Kensey ............ A61B 17/0057 606/213 |
| 2001/0044638 A1 | 11/2001 | Levinson et al. |
| 2001/0049486 A1 | 12/2001 | Evans et al. |
| 2002/0077600 A1 | 6/2002 | Sirimanne |
| 2002/0156455 A1 | 10/2002 | Barbut |
| 2003/0004543 A1 | 1/2003 | Gleeson et al. |
| 2003/0036755 A1 | 2/2003 | Ginn |
| 2003/0093093 A1 | 5/2003 | Modesitt et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0251162 A1 | 11/2005 | Rothe et al. |
| 2005/0267520 A1 | 12/2005 | Modesitt |
| 2006/0052750 A1* | 3/2006 | Lenker ............. A61M 27/008 604/164.01 |
| 2006/0064124 A1 | 3/2006 | Zhu et al. |
| 2006/0106338 A1 | 5/2006 | Chang |
| 2006/0111741 A1 | 5/2006 | Nardella |
| 2006/0167476 A1 | 7/2006 | Burdulis et al. |
| 2006/0200191 A1 | 9/2006 | Zadno-Azizi |
| 2006/0282088 A1 | 12/2006 | Ryan |
| 2006/0287673 A1 | 12/2006 | Brett et al. |
| 2007/0198049 A1 | 8/2007 | Barbut |
| 2007/0270888 A1 | 11/2007 | Barrientos |
| 2008/0045979 A1 | 2/2008 | Ma |
| 2008/0058839 A1 | 3/2008 | Nobles et al. |
| 2008/0097479 A1 | 4/2008 | Boehlke et al. |
| 2008/0140010 A1 | 6/2008 | Kennedy et al. |
| 2008/0188890 A1 | 8/2008 | Weitzner et al. |
| 2008/0221614 A1 | 9/2008 | Mas |
| 2008/0287967 A1 | 11/2008 | Andreas et al. |
| 2008/0312686 A1 | 12/2008 | Ellingwood |
| 2009/0018455 A1 | 1/2009 | Chang |
| 2009/0024072 A1 | 1/2009 | Criado et al. |
| 2009/0143789 A1 | 6/2009 | Houser |
| 2009/0198172 A1 | 8/2009 | Garrison et al. |
| 2009/0254166 A1 | 10/2009 | Chou et al. |
| 2010/0042118 A1 | 2/2010 | Garrison et al. |
| 2010/0191169 A1 | 7/2010 | Chang |
| 2010/0191170 A1 | 7/2010 | Chang |
| 2010/0204684 A1 | 8/2010 | Garrison et al. |
| 2010/0217276 A1 | 8/2010 | Garrison et al. |
| 2010/0228269 A1 | 9/2010 | Garrison et al. |
| 2010/0280431 A1 | 11/2010 | Criado et al. |
| 2011/0004147 A1 | 1/2011 | Renati et al. |
| 2011/0034986 A1 | 2/2011 | Chou et al. |
| 2011/0166496 A1 | 7/2011 | Criado et al. |
| 2011/0166497 A1 | 7/2011 | Criado et al. |
| 2013/0317481 A1 | 11/2013 | Ellingwood et al. |
| 2014/0058414 A1 | 2/2014 | Garrison et al. |
| 2014/0135661 A1 | 5/2014 | Garrison et al. |
| 2014/0296769 A1 | 10/2014 | Hyde et al. |
| 2014/0296868 A1 | 10/2014 | Garrison et al. |
| 2015/0025616 A1 | 1/2015 | Chang |
| 2015/0080942 A1 | 3/2015 | Garrison et al. |
| 2015/0141760 A1 | 5/2015 | Chou et al. |
| 2015/0150562 A1 | 6/2015 | Chang |
| 2015/0174368 A1 | 6/2015 | Garrison et al. |
| 2015/0327843 A1 | 11/2015 | Garrison |
| 2016/0128688 A1 | 5/2016 | Garrison et al. |
| 2016/0158044 A1 | 6/2016 | Chou et al. |
| 2016/0158502 A1 | 6/2016 | Kume et al. |
| 2016/0166804 A1 | 6/2016 | Garrison et al. |
| 2016/0242764 A1 | 8/2016 | Garrison et al. |
| 2016/0271315 A1 | 9/2016 | Chang |
| 2016/0271316 A1 | 9/2016 | Criado et al. |
| 2016/0279379 A1 | 9/2016 | Chang |
| 2016/0296690 A1 | 10/2016 | Kume et al. |
| 2016/0317288 A1 | 11/2016 | Rogers et al. |
| 2017/0043141 A1 | 2/2017 | Kume et al. |
| 2017/0136212 A1 | 5/2017 | Garrison et al. |
| 2017/0209260 A1 | 7/2017 | Garrison et al. |
| 2017/0296798 A1 | 10/2017 | Kume et al. |
| 2017/0312491 A1 | 11/2017 | Ryan et al. |
| 2017/0354523 A1 | 12/2017 | Chou et al. |
| 2017/0354803 A1 | 12/2017 | Kume et al. |
| 2017/0361072 A1 | 12/2017 | Chou et al. |
| 2017/0368296 A1 | 12/2017 | Chang |
| 2018/0008294 A1 | 1/2018 | Garrison et al. |
| 2018/0154063 A1 | 6/2018 | Criado et al. |
| 2018/0185614 A1 | 7/2018 | Garrison et al. |
| 2018/0235789 A1 | 8/2018 | Wallace et al. |
| 2018/0289884 A1 | 10/2018 | Criado et al. |
| 2019/0105439 A1 | 4/2019 | Criado et al. |
| 2019/0150916 A1 | 5/2019 | Hentges et al. |
| 2019/0175885 A1 | 6/2019 | Kume et al. |
| 2019/0231962 A1 | 8/2019 | Criado et al. |
| 2019/0254680 A1 | 8/2019 | Chang |
| 2019/0262530 A1 | 8/2019 | Criado et al. |
| 2019/0269538 A1 | 9/2019 | Chou et al. |
| 2019/0350568 A1 | 11/2019 | Garrison |
| 2019/0366070 A1 | 12/2019 | Kume et al. |
| 2019/0388654 A1 | 12/2019 | Chou et al. |
| 2020/0009406 A1 | 1/2020 | Garrison et al. |
| 2020/0015826 A1 | 1/2020 | Chang |
| 2020/0016321 A1 | 1/2020 | Criado et al. |
| 2020/0038576 A1 | 2/2020 | Garrison et al. |
| 2020/0054871 A1 | 2/2020 | Ryan et al. |
| 2020/0108221 A1 | 4/2020 | Chang |
| 2020/0113587 A1 | 4/2020 | Garrison et al. |
| 2020/0170637 A1 | 6/2020 | Garrison et al. |
| 2020/0171277 A1 | 6/2020 | Garrison et al. |
| 2020/0282127 A1 | 9/2020 | Garrison et al. |
| 2020/0297912 A1 | 9/2020 | Criado et al. |

FOREIGN PATENT DOCUMENTS

| | | |
|---|---|---|
| JP | H07-265412 A | 10/1995 |
| JP | H08-071161 A | 3/1996 |
| JP | 10-052490 A | 2/1998 |
| JP | H10-033666 A | 2/1998 |
| JP | 2001-523492 A | 11/2001 |
| JP | 2002-522149 A | 7/2002 |
| JP | 2002-543914 A | 12/2002 |
| JP | 2003-521299 A | 7/2003 |
| JP | 2007-301326 A | 11/2007 |
| WO | WO-99/25419 A | 5/1999 |
| WO | WO-00/09028 A1 | 2/2000 |
| WO | WO-00/56223 A1 | 9/2000 |
| WO | WO-00/69350 A1 | 11/2000 |
| WO | WO-00/76390 A2 | 12/2000 |
| WO | WO-01/54588 A1 | 8/2001 |
| WO | WO-02/096295 A1 | 12/2002 |
| WO | WO-03/071955 A2 | 9/2003 |
| WO | WO-2004/060169 A2 | 7/2004 |
| WO | WO-2005/051206 A1 | 6/2005 |
| WO | WO-2006/128017 A2 | 11/2006 |
| WO | WO-2009/012473 A3 | 1/2009 |
| WO | WO-2009/099764 A1 | 8/2009 |
| WO | WO-2009/100210 A1 | 8/2009 |
| WO | WO-2010/019719 A2 | 2/2010 |
| WO | WO-2012/021406 A2 | 2/2012 |

(56) References Cited

OTHER PUBLICATIONS

Bergeron, P. (2015, First Published Feb. 1, 2015 Research Article Find in PubMed). "Direct Percutaneous Carotid Access for Carotid Angioplasty and Stenting." Journal of Endovascular Therapy, 22(1), 135-138. https://doi.org/10.1177/1526602814564362.
Bergeron, P., et al. (1999, First Published May 1, 1999 Research Article). "Percutaneous Stenting of the Internal Carotid Artery: The European Cast I Study. Journal of Endovascular Therapy." 6(2), 155-159. https://doi.org/10.1177/152660289900600207.
Bettmann, M. et al., "Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association". Circulation Journal of the American Heart Association. 1998. 97:121-123. Retrieved Feb. 16, 2012.
Bhatt, D. L., R. E. Raymond, et al. (2002). "Successful "preclosure" of 7Fr and 8Fr femoral arteriotomies with a 6Fr suture-based device (the Multicenter Interventional Closer Registry)." Am J Cardiol 89(6): 777-9.
Blanc, R., C. Mounayer, et al. (2002). "Hemostatic closure device after carotid puncture for stent and coil placement in an intracranial aneurysm: technical note." AJNR Am J Neuroradiol 23(6): 978-81.
Blanc, R., M. Piotin, et al. (2006). "Direct cervical arterial access for intracranial endovascular treatment." Neuroradiology 48(12): 925-9.
Chang, D.W., et al., "A new approach to carotid angioplasty and stenting with transcervical occlusion and protective shunting: Why it may be a better carotid artery intervention", J Vasc Surg 2004; 39:994-1002.
Criado et al. (2004). "Transcervical carotid artery angioplasty and stenting with carotid flow reversal: Surgical technique" J. Vasc. Surg. 18:257-261.
Criado et al. (2004). "Transcervical carotid stenting with internal carotid artery flow reversal: Feasibility and preliminary results" J. Vasc. Surg. 40:476-483.
Criado, F.J., et al., Access strategies for carotid artery intervention. J Invasive Cardiol, 2000. 12(1): p. 61-8.
Criado, M.D., et al. (2004) "Carotid angioplasty with internal carotid artery flow reversal is well tolerated in the awake patient" Journal of Vascular Surgery, 40(1):92-7.
Henry et al. (1999) "Carotid stenting with cerebral protection: First clinical experience using the PercuSurge GuardWire System" *J. Endovasc. Surg.* 6:321-331.
Hoffer et al. "Percutaneous Arterial Closure Devices" J. Vasc. Interv. Radiol. 14:865-885 (2003).
Howell, M., K. Doughtery, et al. (2002). "Percutaneous repair of abdominal aortic aneurysms using the AneuRx stent graft and the percutaneous vascular surgery device." Catheter Cardiovasc Interv 55(3): 281-7.
Massiere, B., A. von Ristow, et al. (2009). "Closure of Carotid Artery Puncture Site With a Percutaneous Device." Ann Vasc Surg. 23(2): 256 e5-7.
Ribo et al. (2006, e-published Sep. 28, 2006). "Transcranial doppler monitoring of transcervical carotid stenting with flow reversal protection: a novel carotid revascularization technique" 37:2846-2849.
Ruiz et al., "Feasibility of patent foramen ovale closure with No. device left behind: first-in-man percutaneous suture closure" Catheterization and Cardiovascular interventions 71:921-926 (2008).
Stejskal, et al., "Experience of 500 Cases of Neurophysiological Monitoring in Carotid Endarterectomy", Acta Neurochir, 2007, 149:681-689.
U.S. Appl. No. 14/227,585, filed Mar. 27, 2014.
U.S. Appl. No. 15/049,637, filed Feb. 22, 2016.
U.S. Appl. No. 15/399,638, filed Jan. 5, 2017.
U.S. Appl. No. 16/171,784, filed Oct. 26, 2018.
U.S. Appl. No. 16/281,311, filed Feb. 21, 2019.
U.S. Appl. No. 16/297,348, filed Mar. 8, 2019.
U.S. Appl. No. 16/299,524, filed Mar. 12, 2019.
U.S. Appl. No. 16/353,492, filed Mar. 14, 2019.
U.S. Appl. No. 16/377,663, filed Apr. 8, 2019.
U.S. Appl. No. 16/513,030, filed Jul. 16, 2019.
U.S. Appl. No. 16/530,783, filed Aug. 2, 2019.
U.S. Appl. No. 16/544,083, filed Aug. 19, 2019.
U.S. Appl. No. 16/880,594, filed May 21, 2020.
U.S. Appl. No. 16/894,474, filed Jun. 5, 2020.
U.S. Appl. No. 16/906,457, filed Jun. 19, 2020.
U.S. Appl. No. 16/939,396, filed Jul. 27, 2020.
U.S. Appl. No. 16/951,767, filed Nov. 18, 2020.
U.S. Appl. No. 16/999,634, filed Aug. 21, 2020.
U.S. Appl. No. 16/999,640, filed Aug. 21, 2020.
U.S. Appl. No. 17/000,004, filed Aug. 21, 2020.
PCT/US2020/058365, Oct. 30, 2020, WO 2021/087363.
PCT/US2020/058588, Nov. 2, 2020, WO 2021/087480.
PCT/US2020/061073, Nov. 180, 2020, WO 2021/102011.

* cited by examiner

VESSEL ACCESS AND CLOSURE ASSIST SYSTEM AND METHOD

REFERENCE TO RELATED APPLICATIONS

This application is a continuation of U.S. application Ser. No. 16/250,825 entitled "VESSEL ACCESS AND CLOSURE ASSIST SYSTEM AND METHOD" filed Jan. 17, 2019, issuing on Apr. 13, 2021 under U.S. Pat. No. 10,973,502, which is a continuation of U.S. application Ser. No. 14/710,400 entitled "VESSEL ACCESS AND CLOSURE ASSIST SYSTEM AND METHOD" filed May 12, 2015 now U.S. Pat. No. 10,182,801 and claims priority to: (1) U.S. Provisional Application Ser. No. 61/994,623 entitled "VESSEL ACCESS AND CLOSURE ASSIST SYSTEM AND METHOD" filed on May 16, 2014; and (2) U.S. Provisional Application Ser. No. 62/074,964 entitled "VESSEL ACCESS AND CLOSURE ASSIST SYSTEM AND METHOD" filed on Nov. 4, 2014, the contents of which are herein incorporated by reference in their entirety.

BACKGROUND

Certain vascular interventions involves the insertion of a procedural sheath through a puncture in an artery. An internal lumen of the procedural sheath provides a passageway for the insertion of an interventional device into the artery and to an area of treatment. In a typical procedure, the procedural sheath is inserted into the artery and an intervention is performed using the interventional device, which is inserted into the artery via the procedural sheath. At the end of the procedure, the procedural sheath is removed from the artery and exchanged with a vessel closure device delivery sheath, which provides a passageway for delivery of a vessel closure device to the opening in the artery.

It is important to achieve hemostasis during the exchange of the procedural sheath with the vessel closure device delivery sheath in order to avoid a loss of blood. Unfortunately, the exchange procedure provides an opportunity for loss of blood and also for damage to the blood vessel as the sheaths are exchanged.

In certain clinical procedures, for example procedures requiring access to the carotid arteries, the consequences of failure to achieve complete hemostasis or causing vessel injury during such an exchange procedure can be extreme. For such transcarotid procedures, if full hemostasis is not achieved, the resultant hematoma may lead to loss of airway passage and/or critical loss of blood to the brain, both of which lead to severe patient compromise and possibly death. Alternately, a vessel injury or dissection may require adjunct repair and lead to prolonged procedure time and risk of complication.

SUMMARY

In view of the foregoing, there is a need for vessel access and closure systems for more efficiently delivering a vessel closure device onto a blood vessel. Disclosed is a vessel access and closure assist system for accessing a vessel to perform a vascular intervention, and then facilitating the delivery of a vessel closure device onto a blood vessel for closing an opening in the wall of the blood vessel. The vessel access and closure assist system disclosed herein includes a procedural introducer sheath that directly couples to a vessel closure device delivery sheath such that the procedural introducer sheath does not have to be exchanged with the vessel closure device delivery sheath, as described in detail below.

In one aspect, a blood vessel access and closure assist system, comprising: a procedural introducer sheath sized to be inserted into an artery, the procedural introducer sheath having an internal lumen for delivery of an interventional device into a blood vessel when the introducer sheath is inserted into an artery; a vessel closure device delivery sheath, the vessel closure device delivery sheath having an internal lumen for use with a vessel closure device applier, the internal lumen adapted to deliver a vessel closure device onto a blood vessel; and wherein the vessel closure device delivery sheath and the procedural sheath fixedly couple to one another to form a single assembly that can be inserted into an artery and wherein a distal end of the procedural sheath extends beyond a distal tip of the closure device delivery sheath when the two sheaths are coupled to one another.

In another aspect, there is disclosed A method of treating an artery, comprising: forming a sheath assembly by coupling a procedural introducer sheath to a vessel closure device delivery sheath, wherein the vessel closure device delivery sheath has an internal lumen for delivery of a vessel closure device onto a blood vessel, and wherein the procedural introducer sheath has an internal lumen for delivery of an interventional device into a blood vessel; inserting the sheath assembly into an artery such that the sheath assembly provides a passageway into the artery; inserting an intervention device into the artery via the passageway formed by the sheath assembly; removing the intervention device from the artery; uncoupling the procedural introducer sheath from the vessel closure device delivery sheath so that the procedural introducer sheath is removed from the artery while the vessel closure device delivery sheath remains in the artery; and using the vessel closure device delivery sheath to deliver a vessel closure device to the artery Other features and advantages should be apparent from the following description of various embodiments, which illustrate, by way of example, the principles of the disclosure.

DETAILED DESCRIPTION

Disclosed is a vessel access and closure assist system for accessing a vessel to perform a vascular intervention, and then facilitating the delivery of a vessel closure device onto a blood vessel for closing the opening in the wall of the blood vessel. The system is configured for use with a procedural sheath that may be as long as 50 cm. It may be used to deliver a vessel closure device to a vessel access site, such as an incision, puncture, penetration or other passage through the blood vessel.

Because most vessel closure device systems are suitable for introducer sheaths 11 cm or shorter, or require special introducer sheaths, such systems need for a separate sheath to deliver the vessel closure device. The vessel access and closure assist system disclosed herein includes a procedural introducer sheath that directly couples to a vessel closure device delivery sheath such that the procedural introducer sheath does not have to be exchanged with the vessel closure device delivery sheath, as described in detail below. In an embodiment, the system is packaged as a kit that includes a procedural introducer sheath, a sheath dilator, an introducer guide wire, and a vessel closure device delivery sheath. In an embodiment, the kit also includes a vessel closure device applier. In an embodiment, the vessel closure device delivery system is configured for use in a transcarotid procedure performed at least partially on a blood vessel located in the neck of a patient, such as the carotid arteries including the common carotid artery.

Figure 1A:
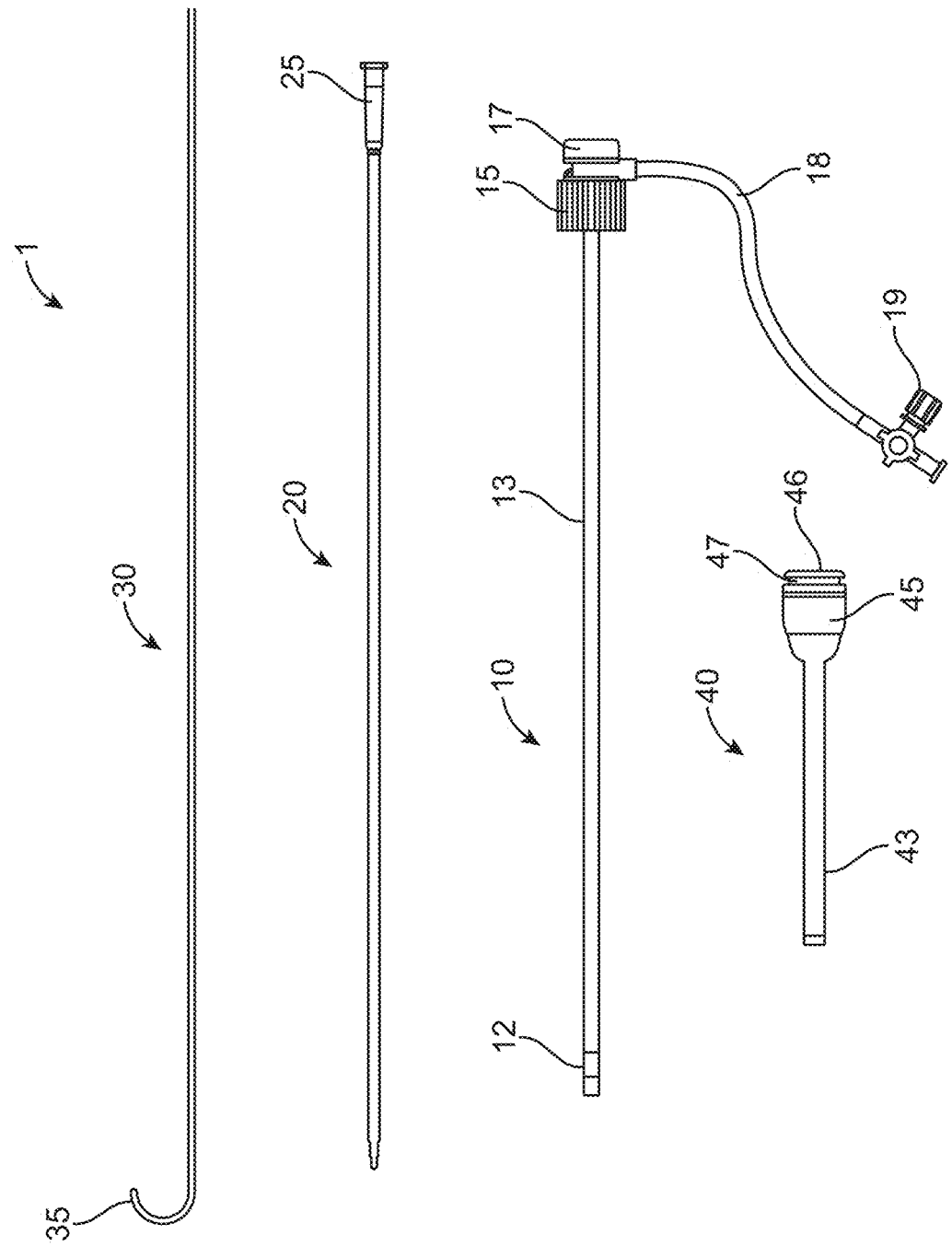
FIGS. 1A and 1B show embodiments of a vessel access and closure assist system.
Figure 1B:
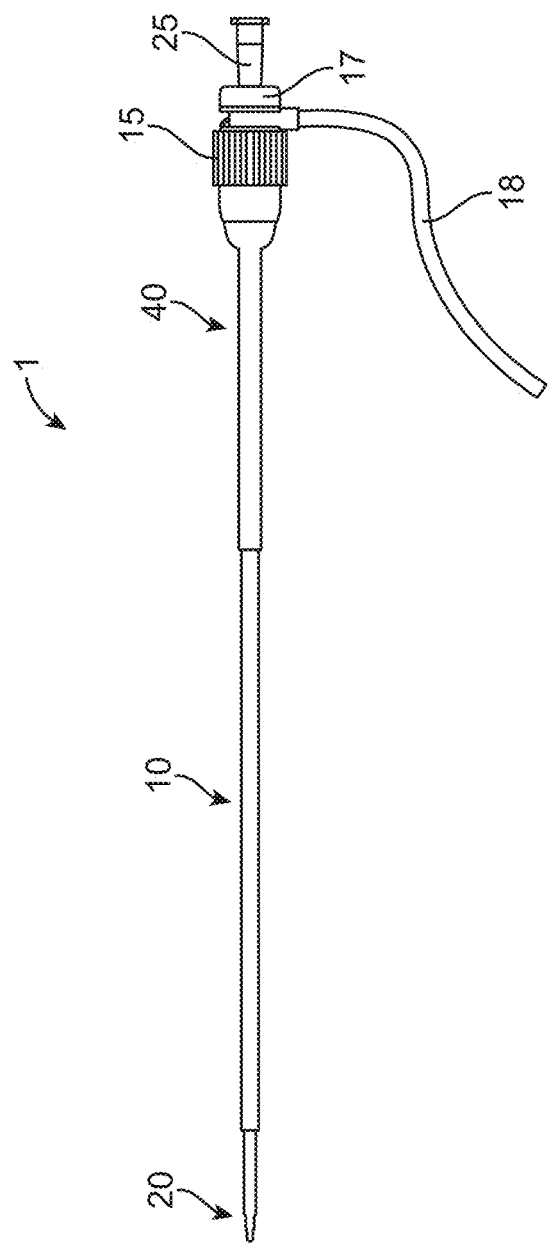

FIGS. 1A and 1B shows an embodiment of a vessel access and closure assist system 1. FIG. 1A shows the system components apart from one another, and FIG. 1B shows the components assembled together prior to use. The system 1 includes at least a pair of sheaths including a procedural introducer sheath 10 and a vessel closure delivery sheath 40. The two sheaths are coupled to one another to form a coupled sheath assembly that can be attached and detached as described further below. The system 1 may also include a sheath dilator 20 which is configured to fit inside the procedural sheath 10. The sheath dilator comprises a dilator body and a proximal hub 25 and is configured to receive an introducer guidewire 30. The dilator body has a tapered distal tip. The system may also include the introducer guide wire 30. The procedural sheath 10, dilator 20, and vessel closure device delivery sheath 40 are configured to be introduced together as a system over the introducer guide wire 30 into the artery as described more fully below.

As shown in FIG. 1A, the procedural sheath 10 comprises a sheath body 13 and a proximal hub 15 that forms a coupling mechanism. In an embodiment there is a distal radiopaque marker 12 on the distal tip of the sheath body 13. There is a hemostasis valve 17 on the proximal end of the proximal hub 15. The hemostasis valve may be a passive seal style valve, or may be a Tuohy Borst style hemostasis valve. The hub also includes a side-arm 18 which terminates with a stopcock 19 and that defines an internal lumen that fluidly communicates with an internal lumen of the procedural sheath 10. Alternately, the proximal hub 15 of the procedural sheath 10 is a female Luer connection which is configured to attach a separate hemostasis valve component, such as a rotating hemostasis valve (RHV) or passive hemostasis valve.

The procedural sheath 10 is sized and shaped to be inserted into a blood vessel via an access site. In this regard, the procedural sheath 10 has an internal lumen that provides a passageway for inserting an interventional device into the blood vessel. As mentioned, the procedural sheath 10 may be adapted to be introduced through an incision or puncture in a wall of a common carotid artery, either an open surgical incision or a percutaneous puncture established, for example, using the Modified Seldinger technique or a micropuncture technique. The working length of the procedural sheath 10 can be in the range from 11 to 50 cm, usually being from 15 cm to 25 cm. The inner diameter may be in the range from 5 Fr (1 Fr=0.33 mm), to 7 Fr, usually being 6 Fr. The working length is the portion of the procedural sheath that is sized and shaped to be inserted into the artery and wherein at least a portion of the working length is actually inserted into the artery during a procedure.

For certain interventions, it may be desirable for the procedural sheath to have a more flexible distal section. In an embodiment, the working length of the procedural sheath 10 is of a length configured to access the proximal internal carotid artery when inserted from an access location in the common carotid artery (CCA), for example 10-15 cm. In another embodiment the device is has a working length configured to access the distal cervical internal carotid artery (ICA) when inserted from the CCA, for example 15-25 cm. In yet another embodiment, the procedural sheath is of a working length configured to access the petrous, cavernous, or terminal portion of the ICA when inserted from the CCA, for example 20-35 cm. In this embodiment, the distal-most portion (which may have a length of about 3 to about 6 cm) of the procedural sheath may be configured to be more flexible to accommodate the curvature in the petreous portion of the ICA. This additional flexibility may be achieved by using a lower durometer outer jacket material in this section. Alternately, the wall thickness of the jacket material may be reduced, and/or the density of the reinforcement layer may be varied to increase the flexibility. For example the pitch of the coil or braid may be stretched out, or the cut pattern in the tubing may be varied to be more flexible. The distal most portion of the procedural sheath may also be tapered or stepped down to a smaller diameter. In an embodiment, the procedural sheath may include multiple sections of flexibility, with increasing flexibility towards the distal end. U.S. patent application Ser. No. 14/569,365 filed Dec. 12, 2014 and U.S. Pat. No. 8,157,760 describe related systems and are both incorporated herein by reference in their entirety.

The procedural sheath 10 may also include a connection to a flow line or shunt which may be connected to a device for passive or active reverse flow. In an embodiment, the flow line has an internal lumen that communicates with an internal lumen of the procedural sheath 10 for shunting blood from the procedural sheath. In an embodiment, the flow line is a side arm or Y-arm that is attached to and extends from the procedural sheath 10 at a location between the distal and proximal ends of the procedural sheath 10.

The vessel closure device delivery sheath 40 comprises an elongated body 43 and a proximal hub 45 which includes a hemostasis valve 47 and an end cap 46 on the proximal region of the elongated body 43. The proximal hub forms a coupling mechanism that couples to the coupling mechanism of the procedural sheath 10. The vessel closure device delivery sheath 40 has an internal lumen such that it can co-axially fit over the procedural sheath 10 and be shorter than the procedural sheath but still suitable for use in percutaneous procedures, for example in a range between 8 to 11 cm. As noted above, most vessel closure device systems are suitable for introducer sheaths 11 cm or shorter. In an embodiment, the vessel closure device delivery sheath 40 has a working length of 8 to 11 cm and the procedural sheath has a minimum working length of 1 cm greater than the length of the vessel closure device delivery sheath 40, with a range of lengths as described above.

For a system 1 to be configurable for vessel closure devices which can be deployed through standard introducer sheaths, for example, the Mynx Vascular Closure Device (Access Closure), the vessel closure devices can be deployed through a vessel closure device delivery sheath 40 with a standard sheath hemostasis valve 47. In some instances, a vessel closure devices require custom delivery sheaths, for instance, the StarClose (Abbott Vascular) and Angioseal (St. Jude Medical) require delivery sheaths with features that couple with the closure device delivery system. Typically, the custom delivery sheaths are packaged with the closure delivery device and delivery system. At the end of the procedure, the procedural sheath is required to be exchanged for the custom delivery sheath to enable closure with the vessel closure system. For a system 1 to be configurable to these devices, the vessel closure device delivery sheath 40 requires corresponding features to enable deployment of these devices.

The internal lumen of the vessel closure device delivery sheath 40 is sized to receive the procedural sheath 10 such that the procedural sheath 10 can be coupled to the vessel closure device delivery sheath 40 by being positioned co-axially inside the vessel closure device delivery sheath 40. In this regard, the procedural sheath 10 is longer than the closure device delivery sheath 40 such that procedural sheath 10 extends out of the distal end of the vessel closure device delivery sheath 40 when the two are coupled as shown in FIG. 1B. The distal tip of the vessel closure device delivery sheath 40 sheath is sized and shaped to create a tight fit and smooth transition between the outer diameter of the procedural sheath 10 and the inner diameter of the vessel closure device delivery sheath 40, such that the insertion of the assembled sheaths is relatively smooth and easy. In this regard, the distal tip of the vessel closure device delivery sheath 40 may be tapered to form a gradual transition between the outer surfaces of the two sheaths.

In an embodiment, system 1 includes features which couple the vessel closure device delivery sheath 40 and the procedural sheath 10 mechanically together, such that when assembled together the sheaths may be inserted as one, single device into the artery at the start of the procedure such that vessel closure device delivery sheath 40 and the procedural sheath 10 are fixed relative to one another. In one example, the procedure sheath has a rotatable collar 15 on the end of its proximal hub with internal elements such as protrusions or threads that can rotationally engage and lock into grooves on the end cap 46 of the vessel closure device delivery sheath.

To assemble the two devices, the procedure sheath 10 is inserted into the vessel closure device delivery sheath 40 until the rotating collar 15 reaches and engages the end cap 46 of the vessel closure device delivery sheath. The collar 15 can be aligned with the end cap 46 so that the internal elements of the collar can slide into the grooves of the end cap, and then rotate so that the two sheaths are now locked and fixed relative to one another. To un-couple the sheaths, the rotating collar 15 is rotated in the opposite direction to disengage the protrusions or threads on the end cap 46. Alternately, the protrusions are on the vessel closure device delivery sheath end cap 46 and the grooves or threads are on the rotating collar. In another example, the end of the procedure sheath hub 15 has a feature which can snap into the end cap 46 of the vessel closure device delivery sheath 40 when the procedure sheath 10 is inserted into the vessel closure device delivery sheath 40. In this example, the two sheaths are pushed together to mechanically engage one another and pulled apart to disengage from one another.

In another embodiment, the vessel closure device delivery sheath 40 may be positioned anywhere that is suitable for the procedure 10 such that the distal tip of the procedure sheath 10 extends beyond the distal tip of the vessel closure device delivery sheath 40, up to the point where the closure sheath hub 45 abuts the procedure sheath hub 15 and can be manipulated and/or used as an unit or system.

The sheath dilator 20 has an internal lumen sized to co-axially receive an introducer guidewire 30. In an embodiment, the guide wire 30 is an 0.038" outer diameter guidewire, and the dilator 20 internal lumen diameter and taper shaped are optimized to provide a smooth transition from the dilator 20 to the guide wire 30. In another embodiment, the guide wire 30 is an 0.035" diameter guidewire, with sheath dilator 20 inner lumen diameter and taper configured accordingly. In another embodiment the guide wire 30 is an 0.018", an 0.016", or an 0.014" OD guide wire, with sheath dilator 20 inner lumen diameter and taper configured accordingly. The guide wire 30 has an atraumatic tip 35 on the distal end. In an embodiment, the guide wire tip 35 has a J-shape. In another embodiment, the guide wire tip 35 is an angled tip. In another embodiment the guide wire has a floppy tip. In an embodiment, the guide wire core is constructed from spring stainless steel. In another embodiment, the guide wire core is constructed from nitinol. In another embodiment, the guide wire core is a combination of stainless steel and nitinol.

Figure 2:
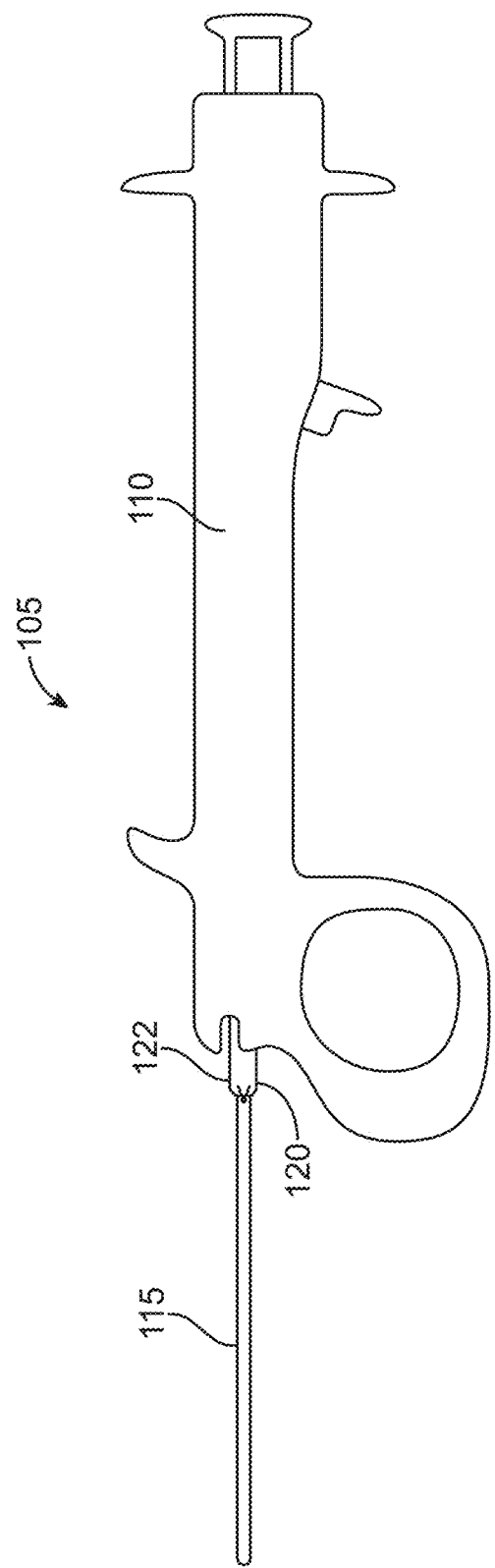
FIG. 2 shows an exemplary vessel closure device applier of a vessel access and closure assist system.
Figure 3:
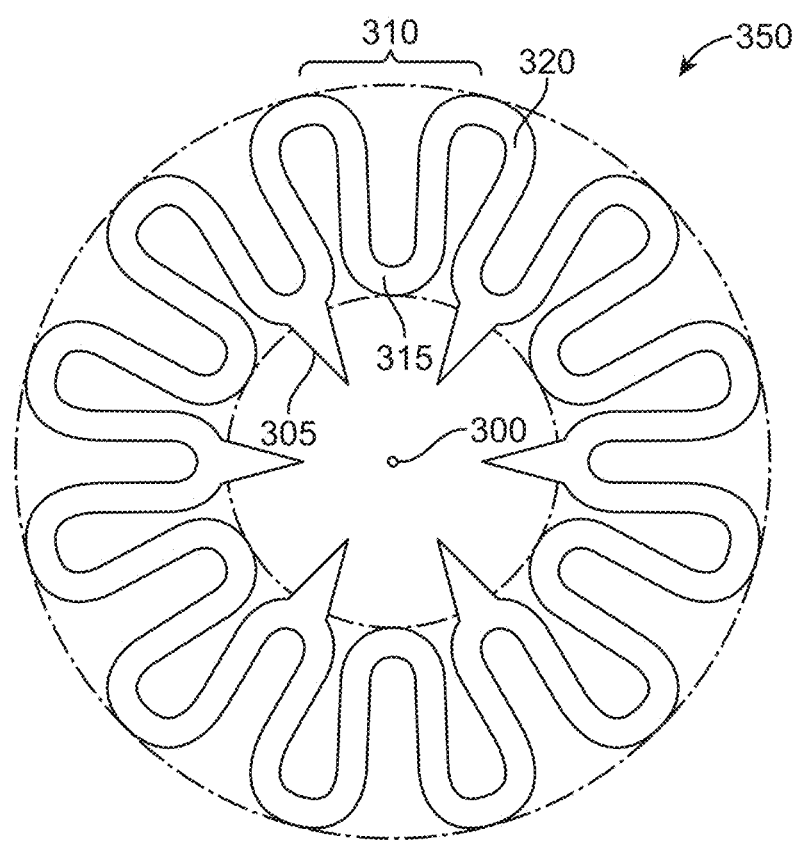
FIG. 3 shows an exemplary blood vessel closure device.

FIG. 2 shows an embodiment of an exemplary vessel closure device applier 105, which is configured to deliver a vessel closure device onto an artery. In an embodiment, the applier 105 is configured to deliver a vessel closure device, such as the type of closure clip described in U.S. patent application Ser. No. 12/713,630 entitled Vessel Closure Clip Device, which is incorporated herein in its entirety. An exemplary vessel closure device 350 is shown in FIG. 3. However, the vessel closure device delivery sheath may work with other types of vessel closure devices and device appliers. In an embodiment, the vessel access and closure assist system 1 includes the vessel closure device applier 105. In another embodiment, the applier 105 is not part of system 1.

As shown in FIG. 2, the applier 105 includes a handle 110, which is sized and shaped to be grasped by a user. An elongated delivery shaft 115 extends outward from a distal end of the handle 110. At the end of the procedure, the procedural sheath 10 is uncoupled and removed from the vessel closure device delivery sheath 40. The shaft 115 of applier 105 is inserted into the inner lumen of the vessel closure device delivery sheath 40 so as to deliver the closure device 350 to the wall of the vessel. In an embodiment, the shaft 115 passes through the sheath 40 until the handle abuts the proximal hub 45 of the vessel closure device delivery sheath 40, at which time the hub 45 can be attached to the handle 110.

FIG. 3 shows an exemplary vessel closure device 350 comprised of a clip for closing an incision. It should be appreciated the clip shown in FIG. 3 is an example and that other types of clips and other types of vessel closure device may be used with the system. The clip is adapted to transition between a cylindrical configuration and a flat or planar configuration. The annular body may include a plurality of looped or curved elements 310 and tines 305 that are connected to one another to form the body. Each looped element 310 may include an inner or first curved region 315 and an outer or second curved region 320. When the clip is in the substantially flat or planar configuration, as shown in FIG. 3, the first curved regions 315 may define an inner periphery of the body and the clip, and the second curved regions 320 may define an outer periphery of the body.

In an embodiment, the applier 105 is configured to deliver the vessel closure clip 350 to the artery. The clip is deployed from applier 105, transitioning from a cylindrical configuration (as stored) to a flat configuration in the vessel wall (post deployment). In this embodiment, the applier includes a tubular housing 122 which contains the vessel closure clip 350 in the cylindrical configuration and is movably coupled to the shaft 115 to deliver the vessel closure clip 350 to the surface of the vessel. That is, the tubular housing 122 moves along the shaft 115. In this embodiment, the tubular housing 122 is larger in diameter than the shaft 115 such that the tubular housing 122 does not fit through the lumen of the vessel closure device delivery sheath 40. Thus, in this embodiment, the elongated body 43 of the vessel closure device delivery sheath 40 is modifiable to be able to accept the applier 105 as the tubular housing 122 is advanced distally to the distal end of the shaft 115 to deliver the vessel closure device.

In an embodiment, the tubular housing 122 splits or tears apart the body 43 of the vessel closure device delivery sheath 40 as the housing 122 with the closure device 350 is advanced to the distal tip of the shaft 115 and the shaft 115 is in the vessel closure device delivery sheath 40. In an embodiment, the applier 105 includes a sharp blade 120 on the distal end of tubular housing 122 to assist in initiation of the split when the proximal hub 45 of the vessel closure device delivery sheath 40 is coupled to the handle 110 of the applier 105. In another embodiment, the elongated body 43 of the vessel closure device delivery sheath 40 radially expandable such that it can stretch to accommodate insertion of the housing 122 into the vessel closure device delivery sheath 40 as the housing 122 is pushed forward to the distal end of the shaft 115. The materials and construction for this sheath can be but is not limited to splittable polymer such as PTFE or polyethylene, or PET, PE or custom extrusion that has been pre-scored with a blade in order to produce a thinner wall section to facilitate the splitting.

Another exemplary vessel closure device is a plug-type closure device and associated closure device applier. This type of device deposits a plug material such as a collagen plug or polymer material against the outside of the vessel access site and typically expands in situ to create hemostasis at the site. Some devices additionally provide temporary, semi-permanent or permanent anchoring to ensure sufficient compression of the plug against the access site to maintain hemostasis. In an embodiment, the applier 105 is configured to deliver a vessel closure device, such as the type of device described in U.S. Pat. No. 5,676,689. In this example, the vessel closure device delivery sheath 40 is configured to be compatible with this plug device applier. For example, features on the device applier will mate with features on the proximal hub 47 of vessel closure device delivery sheath 40 to ensure that the applier is in the correct orientation with respect to the sheath, The vessel closure device delivery sheath 40 may also include features such as blood inlet holes to ensure that the sheath is in the correct position with respect to the vessel to accurately deposit the plug.

An exemplary method of using the vessel access and closure assist system is now described, as shown in FIGS. 4A-4D. An introducer guidewire 30 is inserted into the blood vessel via the access site using standard techniques, for example a modified Seldinger or micropuncture technique. The sheath dilator 20 is inserted into the procedural sheath 10, until the dilator hub 25 snaps into or otherwise engages the procedural sheath hub 15.

Figure 4A:
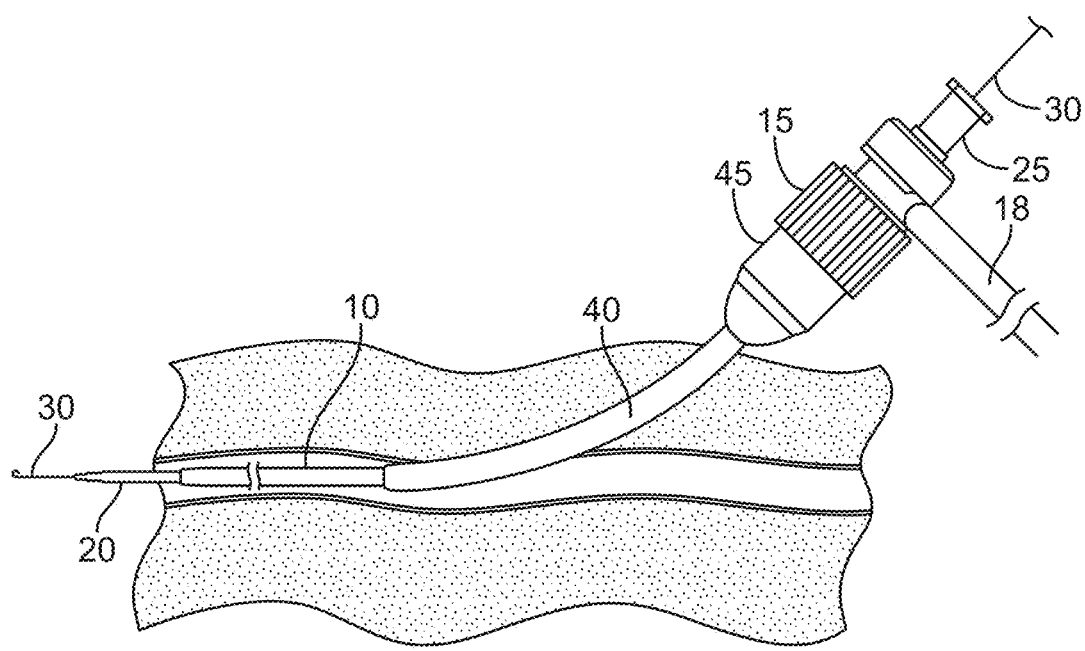
FIGS. 4A-D shows use of the system in accessing a vessel and then assisting in closing the vessel using exemplary closure device.
Figure 4B:
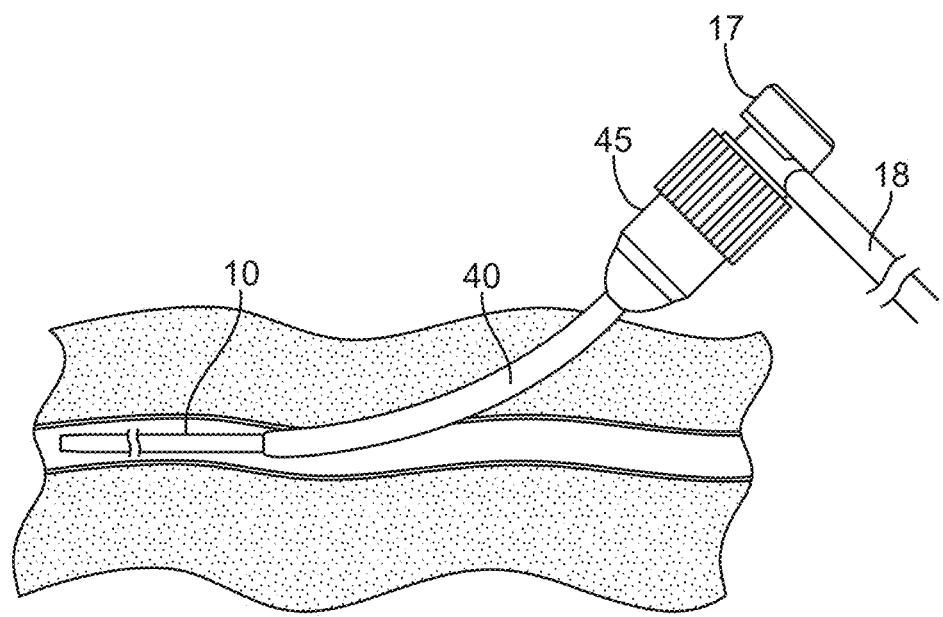

The procedural sheath 10 is then coupled to the vessel closure device delivery sheath 40 by inserting the procedural sheath 10 into the vessel closure device delivery sheath 40 such that the two are co-axially aligned. Alternately, the vessel closure device delivery sheath 40 is inserted into the procedural sheath 10 in another embodiment. The rotating collar 15 on the procedural sheath engages the end cap 46 on the vessel closure device delivery sheath hub 45 and is rotated to lock the two sheaths together such that they are immobilized relative to one another. When coupled, the two sheaths form a coupled sheath assembly wherein a distal end of the procedural sheath 10 extends out of and/or distally past a distal end of the vessel closure device delivery sheath 40, as shown in FIG. 1B. The coupled sheaths and dilator are then inserted into the blood vessel as a single assembly over the guide wire 30 through the access site into to the blood vessel. This step is shown in FIG. 4A. Once in the blood vessel, the guide wire 30 and sheath dilator 20 are removed, leaving the two coupled sheaths as shown in FIG. 4B. In this manner, the coupled sheaths (procedure sheath 10 and vessel closure device delivery sheath 40) provide a passageway into the blood vessel whereby hemostasis is maintained by hemostasis valves 47 and 17. As mentioned, the access site may be a transcarotid access site such as in the region of the carotid arteries.

The side arm 18 and stopcock 19 may be used to flush the internal lumen of the procedural sheath 10 as well as inject contrast as desired during the procedure. An interventional device (which may also referred to as a procedural device), such as a balloon catheter, stent delivery catheter, aspiration catheter, thrombectomy catheter, or other working catheter, can then be introduced into the artery via the internal lumens of the coupled sheaths. The devices may be used in conjunction with intermediate or distal access catheters, microcatheters, guide wires, and the like. In this regard, the internal lumen of the procedural sheath 10 provides a passageway for insertion of interventional devices. In an example, the catheter can be used to treat the plaque such as to deploy a stent into a carotid or cerebral artery. As mentioned, a stent delivery catheter and method is just an example of an intervention that can be used in conjunction with the vessel access and closure assist system. Other interventions are possible such as, for example, intracranial balloon angioplasty, intracranial thrombectomy, treatment of intracerebral aneurysms, arteriovenous malformations, or other intracerebral procedures.

Figure 4C:
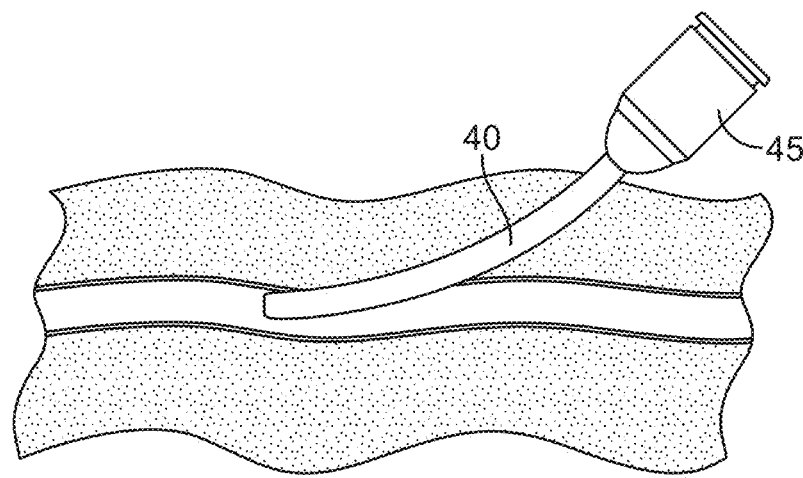

At the conclusion of the intervention, the interventional device or devices are then removed from the coupled sheath assembly. The procedural sheath 10 and vessel closure device delivery sheath 40 are then uncoupled either by rotating a connector attached to sheath 10 at hub 15 or by detaching a snap interface at hub 15 from the procedural sheath 10 and pulling sheath 10 out of the vessel closure device delivery sheath 40. The vessel closure device delivery sheath 40 then remains in the artery as shown in FIG. 4C. Advantageously, the vessel closure device delivery sheath 40 is already positioned in the artery due to the vessel closure device delivery sheath 40 and the procedural sheath 10 being pre-coupled to one another and positioned in the artery as a single assembly. This eliminates the step of having to perform an exchange procedure where the procedural sheath 10 is removed from the artery and then the vessel closure device delivery sheath 40 is inserted into the artery. In certain clinical procedures, for example procedures requiring access to the carotid arteries, the consequences of failure to achieve complete hemostasis or causing vessel injury during such an exchange procedure can be extreme. In this instance, if full hemostasis is not achieved, the resultant hematoma may lead to loss of airway passage and/or critical loss of blood to the brain, both of which lead to severe patient compromise and possibly death. Alternately, a vessel injury or dissection may require adjunct repair and lead to prolonged procedure time and risk of complication.

Figure 4D:
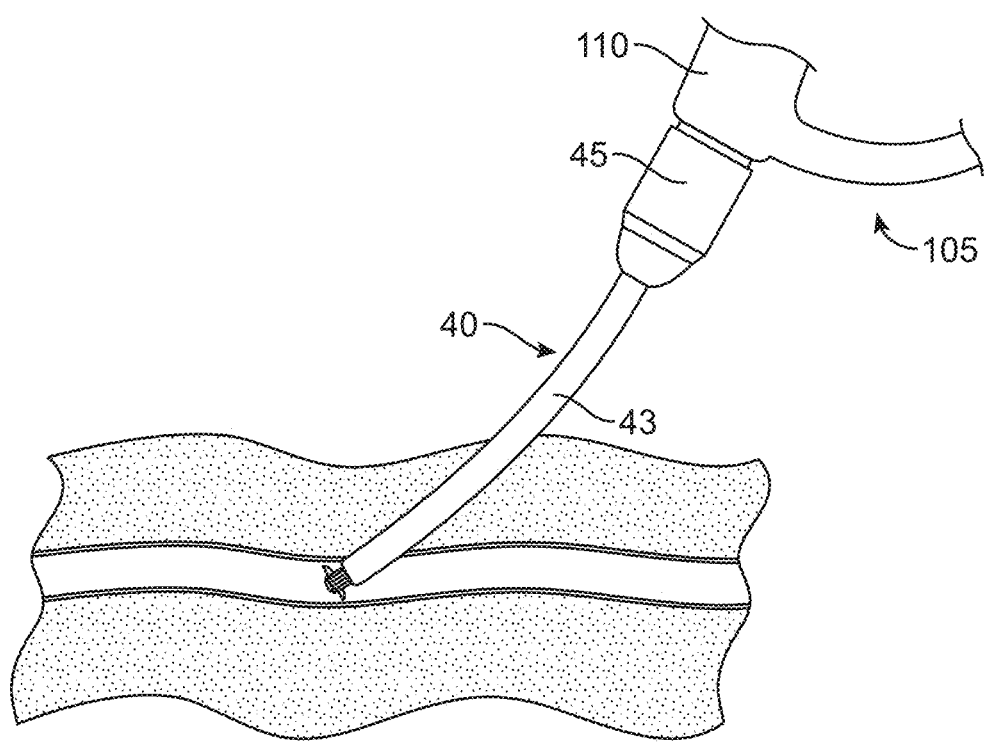

With the vessel closure device delivery sheath 40 positioned in the artery, the shaft 115 (FIG. 2) of the applier 105 is then inserted into the vessel closure device delivery sheath 40 such that the sheath hub 45 is coupled to the distal end of the handle 110, as shown in FIG. 4D. The vessel closure device delivery sheath 40 provides a passageway for delivery of the vessel closure device such as a closure clip. As mentioned, the tubular housing 122 (FIG. 2) can split or tear apart the body 43 of the vessel closure device delivery sheath 40 as the closure device is delivered. In another embodiment, the elongated body 43 of the vessel closure device delivery sheath 40 radially expands 40 as the tubular housing 122 (FIG. 2) travels toward the closure location and the closure device is delivered.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A blood vessel access and closure assist system, comprising:
   a procedural introducer sheath sized to be inserted into an artery, the procedural introducer sheath having an internal lumen for delivery of an interventional device into a blood vessel when the introducer sheath is inserted into an artery;
   a vessel closure device delivery sheath, the vessel closure device delivery sheath having an internal lumen for use with a vessel closure device applier, the internal lumen adapted to deliver a vessel closure device onto a blood vessel;
   the vessel closure device; and
   the vessel closure device applier, wherein the vessel closure device applier has an elongated delivery shaft and a sharpened housing that contains the vessel closure device and wherein the sharpened housing is configured to tear the vessel closure device delivery sheath and advance the vessel closure device toward a distal tip of the elongated delivery shaft of the vessel closure device applier;
   wherein the vessel closure device delivery sheath and the procedural sheath fixedly couple to one another to form a single assembly that can be inserted into an artery and wherein a distal end of the procedural sheath extends beyond a distal tip of the closure device delivery sheath when the two sheaths are coupled to one another.

2. A system as in claim 1, wherein the procedural introducer sheath couples to the vessel closure device delivery sheath by being inserted into the internal lumen of the vessel closure device delivery sheath.

3. A system as in claim 1, wherein the procedural sheath includes a first hub and the vessel closure device delivery sheath includes a second hub, and wherein the first and second hubs couple to one another to immobilize the procedural sheath relative to the vessel closure device delivery sheath.

4. A system as in claim 3, wherein the first and second hubs couple to one another via a threaded connection.

5. A system as in claim 3, wherein the first and second hubs couple to one another via a snap fit.

6. A system as in claim 1, wherein the vessel closure device is a vessel closure clip.

7. A system as in claim 1, further comprising a sheath dilator.

8. A system as in claim 1, further comprising an introducer guide wire.

9. A system as in claim 1, further comprising a package that contains the vessel closure device delivery sheath, the procedural introducer sheath, a sheath dilator, and an introducer guide wire.

* * * * *